(12) United States Patent
Krusenklaus

(10) Patent No.: US 6,454,733 B1
(45) Date of Patent: Sep. 24, 2002

(54) FOOT STRAP

(76) Inventor: John H. Krusenklaus, 7260 Bricey La., Knoxville, TN (US) 37918

( * ) Notice: Subject to any disclaimer, the term of this patent is extended or adjusted under 35 U.S.C. 154(b) by 0 days.

(21) Appl. No.: 09/794,777

(22) Filed: Feb. 27, 2001

(51) Int. Cl.[7] ................................................ A61F 5/00
(52) U.S. Cl. ............................ 602/30; 602/75; 128/882
(58) Field of Search .................... 128/869, 876, 128/882, 892, 893; 602/23, 30, 75

(56) References Cited

U.S. PATENT DOCUMENTS

| 1,156,621 A | 10/1915 | O'Dwyer |
| 1,283,335 A | 10/1918 | Shillcock |
| 1,365,512 A | 1/1921 | Lewis |
| 1,443,844 A | 1/1923 | Jensen |
| 1,462,534 A | 7/1923 | Condylis et al. |
| 1,465,970 A | 8/1923 | Cleveland et al. |
| 1,788,852 A | 1/1931 | Arthur |
| 2,292,643 A | 8/1942 | Layana |
| 2,358,966 A | 9/1944 | Einstoss |
| 2,708,930 A | 5/1955 | Lowman |
| 3,383,708 A | 5/1968 | Pappas |
| 3,504,668 A | 4/1970 | Boudon |
| 3,699,959 A | 10/1972 | Garrahan et al. |
| 3,867,930 A | 2/1975 | Brown |
| 4,084,586 A | 4/1978 | Hettick |
| 4,392,487 A | 7/1983 | Selner et al. |
| 4,559,934 A | 12/1985 | Philipp |
| 5,399,155 A | 3/1995 | Strassburg et al. |
| 5,620,413 A | 4/1997 | Olson |

FOREIGN PATENT DOCUMENTS

| DE | 4014728 | 11/1990 |
| DE | 4309740 | 10/1993 |

OTHER PUBLICATIONS

Abnormal Biomechanics of the Foot and Ankle by Robert Donatelli, MA, PT pp. 11–16 JOSPT vol. 9, No. 1.

Primary Examiner—Michael A. Brown
(74) Attorney, Agent, or Firm—Luedaka, Neely & Graham PC

(57) ABSTRACT

A device for treating conditions associated with excessive pronation of the subtalar joint of a human foot, including a substantially T-shaped strap member having an elongate leg section and a head section substantially transverse to the leg section. The head section is configured so as to be positionable to substantially wrap around a toe of the human foot, such as the big toe.

8 Claims, 3 Drawing Sheets

FOOT STRAP

FIELD OF THE INVENTION

The present invention relates to orthotic devices. More particularly, the invention relates to devices for providing foot comfort.

BACKGROUND AND SUMMARY OF THE INVENTION

The hindfoot of the human foot is made up of two bones known as the talus and the calcaneus or heel bone. The talus connects to the calcaneus at the subtalar joint. A variety of foot discomforts have been attributed to excessive pronation (calcaneal eversion internal rotation and palntar flextion of the talus) of the subtalar joint including plantar fasciitis, heel spurs, shin splints, turf toe, arthritis of the big toe (hallux limitus and hallux rigidus) bunions and the like.

Accordingly it is an object of the present invention to provide a device for treating conditions associated with excessive pronation of the subtalar joint.

Still another object of the present invention is to provide a device of the character described that is suitable for providing foot comfort.

Yet another object of the invention is to provide a device of the character described that may be worn while a user is wearing shoes.

A still further object of the invention is to provide a device of the character described that is economical to produce and uncomplicated in configuration.

With regard to the foregoing and other objects, the present invention is directed to a device for treating conditions associated with excessive pronation of the subtalar joint and midtarsal joint of a human foot which results in instability of the foot during the gait cycle.

In a preferred embodiment, the orthotic device includes a substantially T-shaped strap member having an elongate leg section and a head section substantially transverse to the leg section. The head section is configured so as to be positionable to substantially wrap around a toe of the human foot, such as the big toe, to maintain it in a desired orientation.

In another aspect, the invention relates to a method for treating conditions associated with excessive pronation of the subtalar joint of a human foot.

In a preferred embodiment, the method includes the steps of providing a strap having a first portion configured for engaging a toe of the foot, positioning the first portion of the strap about the toe of the foot and securing the first portion adjacent the toe, exerting a tension on the strap so as to urge the toe to a desired orientation, and securing the strap adjacent the foot so as to maintain the tension on the strap so that the toe remains in the desired orientation.

BRIEF DESCRIPTION OF THE DRAWINGS

Further advantages of the invention will become apparent by reference to the detailed description of preferred embodiments when considered in conjunction with the figures, which are not to scale, wherein like reference numbers, indicate like elements through the several views, and wherein.

DETAILED DESCRIPTION

Figures 1, 1A:
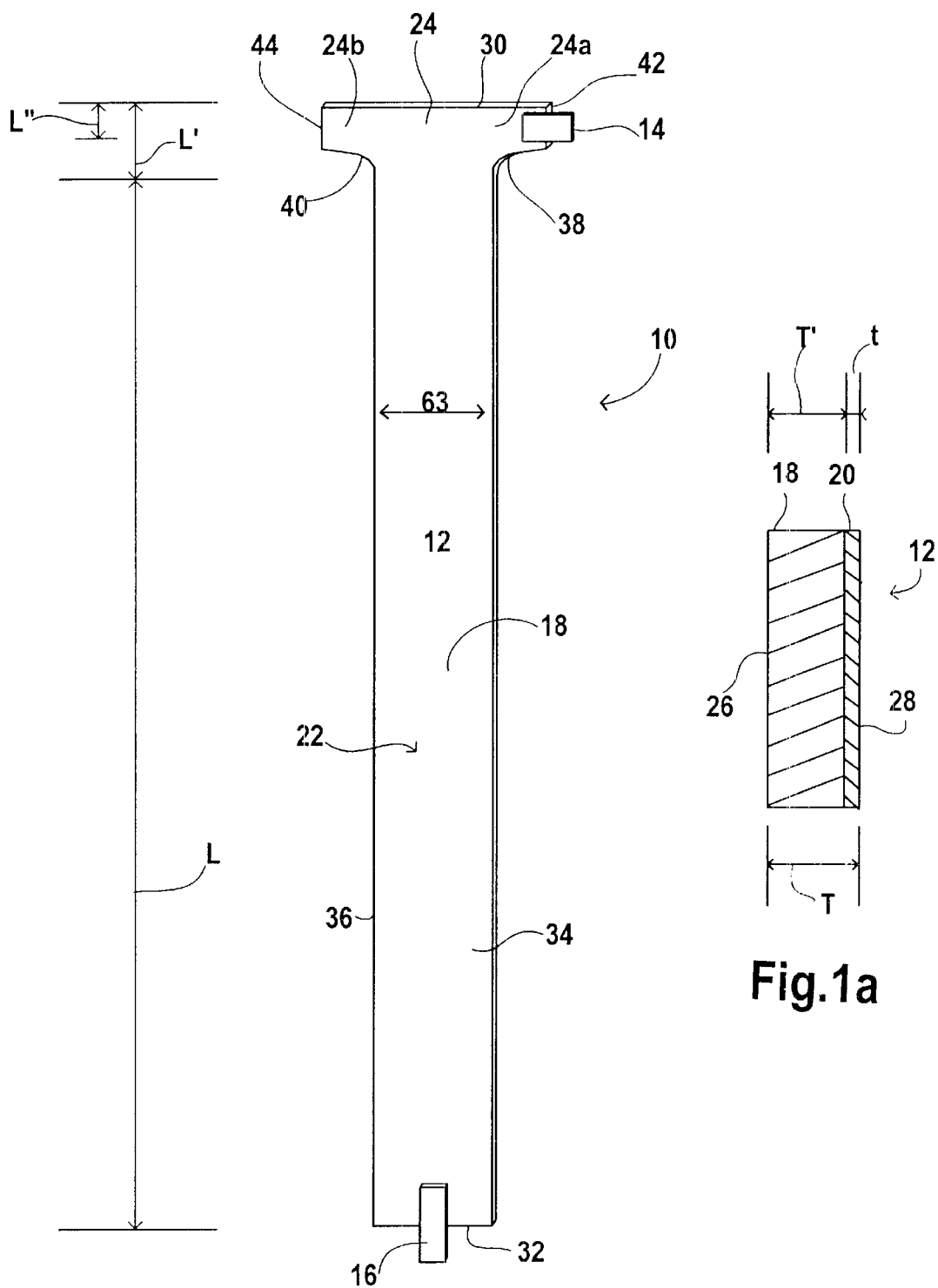
FIG. 1 is a top plan view of a strap system in accordance with a preferred embodiment of the invention and FIG. 1 a is a cross-sectional view of a strap member of the system of FIG. 1.

With initial reference to FIG. 1, the invention relates to a strap system 10 that is particularly suitable for providing comfort to a human foot by controlling pronation of the foot and by cushioning the foot. The strap system 10 includes a strap member 12 and fastening members 14 and 16.

The strap member 12 is preferably of one-piece construction and made of a soft and substantially elastic material. A preferred material is an open-celled, elastomeric, non-latex foam material 18 having a hook-receptive fabric 20 on one surface (FIG. 1a). A preferred material of this type is available under the trademark FABRIFOAM from Fabrifoam Products of Exton, Pa. However, virtually any suitable substantially elastic material may be used to provide the strap member 12.

The strap member 12 is substantially T-shaped, having a leg section 22 having a length L and a width W, and a "T" or head section 24 having a width W' defined by wing portions 24a and 24b that is greater than the width W and a length L' that is substantially less than the length L of the leg section 22. The strap member 18 has a thickness T, with the foam material having a thickness T' and the fabric 20 having a thickness t.

Use of the preferred FABRIFOAM material renders the strap member 12 with a foam surface 26 and an opposite fabric surface 28. T-strap member 12 also includes end 30 terminating the head section 24 and an opposite end 32 terminating the leg section 22. The leg section includes opposite sides 34 and 36. Opposite curved sides 38 and 40, preferably connect the leg section to the head section 24. Opposite sides 42 and 44 extend between the curved sides 38 and 40, respectively, and the end 30. The sides 42 and 44 have a length L".

For the purpose of example only, the strap member 12 may have the following dimensions:

| Reference numeral | Dimension (inches) |
| --- | --- |
| L | 33 |
| L' | 1.5 |
| L" | 0.5 |
| W | 2.5 |
| W' | 5 |
| T | 5/64 |
| T' | 1/16 |
| t | 1/64 |

However, it will understood that the strap member 12 may be provided in various other dimensions suitable for the purpose.

The fastening members 14 and 16 are preferably short lengths of a plastic sheet material having a plurality of hook members defined on one surface thereof of a type commonly used for matingly engaging hook and loop material. The purpose of the fastening members is to span between adjacent portions of the strap member 12 and maintain them in a desired orientation. As will be appreciated, tape, adhesive strips or other fasteners could be used as well as tucking or tying of the strap member.

Turning now to FIGS. 2–7, there are shown preferred steps in the installation of the strap system of FIG. 1 onto a user's foot 50 having a first or big toe 51, second toe 52, heel 53 and inner and outer heel portions 53a and 53b, top portion 54, bottom portion 55, arch 56, inner and outer front portions 57a and 57b, and inner and outer sides 58a and 58b.

Figure 2:
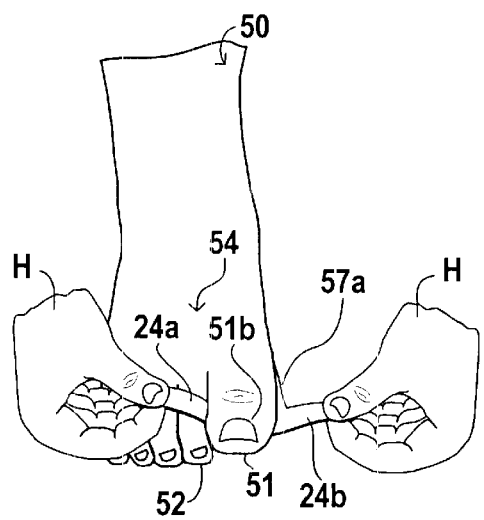
FIGS. 2–7 are perspective views showing installation of the strap system of FIG. 1 onto a user's foot.

Initially, as shown in FIG. 2, the "T" section 24 of the strap member 22 may be positioned (as by a user's hands H) adjacent bottom surface 51a of the big toe 51 with the foam material 18 adjacent the skin of the big toe 51. The wing portions 24a and 24b are on either side of the big toe 51, with wing portion 24a being positioned between the big toe 51 and the second toe 52.

Figure 3:
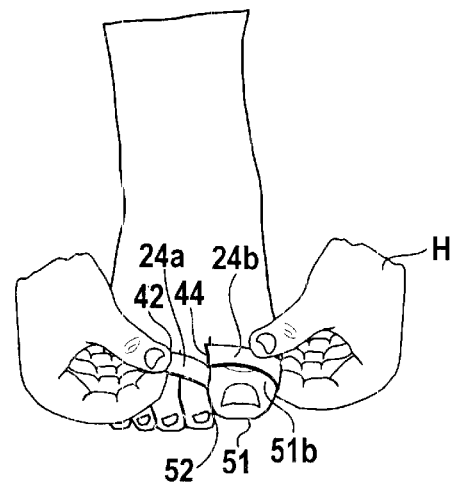

With reference to FIG. 3, the wing portion 24b is wrapped over dorsal and medial areas or knuckle portion 51b of the big toe 51. The wing portion 24a is then wrapped over the wing portion 24b and the fastener member 14 positioned to span across the overlap of the wing portions 24a and 24b and engage the surface 28 thereof to maintain the wing portions 24a and 24b in the overlapped orientation around the big toe 51.

Figure 4:
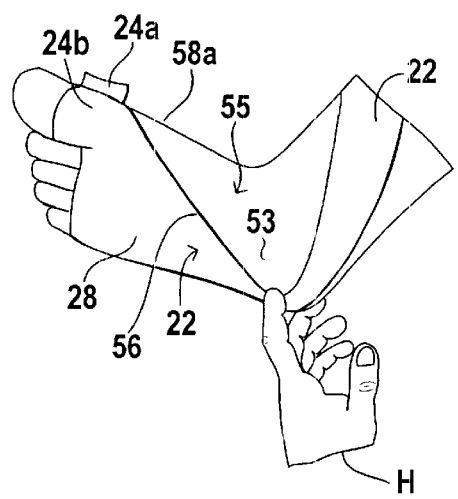

Turning to FIG. 4, the leg section 22 of the strap member 12 is positioned so that it extends from the thus secured head section 24 adjacent the big toe 51 along the bottom portion 55 of the foot 50 towards outer portion 53b of the heel 53 opposite from the big toe 51, preferably maintaining sufficient tension to comfortably urge the toe 51 in a desired orientation. For example, depending upon the condition to be treated, tension may be applied in different degrees to the strap member 12 to urge the big toe into a straightened orientation or to flex the big toe downwardly, or to place it in a neutral or slightly medial alignment.

Figure 5:
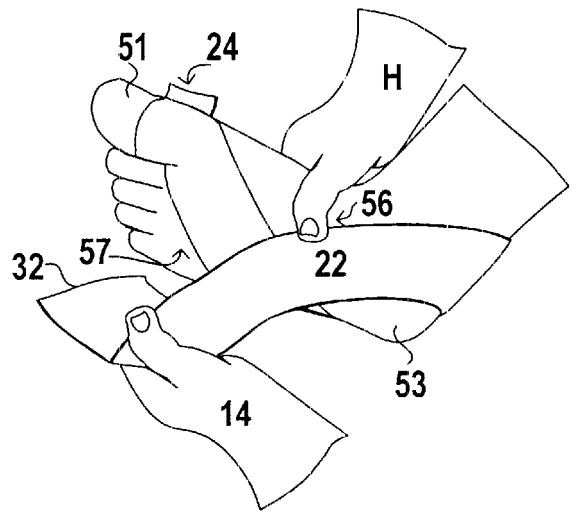

As shown in FIG. 5, the leg section 22 may then be pulled around the back of the heel 53, in a "figure 8" orientation through the arch 56 of the foot 50 and across the bottom portion 55 of the foot 50 toward the outer front portion 57a of the foot 50.

Figure 6:
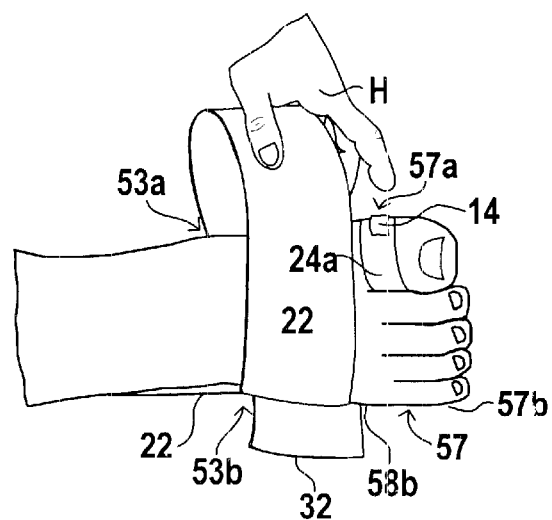
Figure 7:
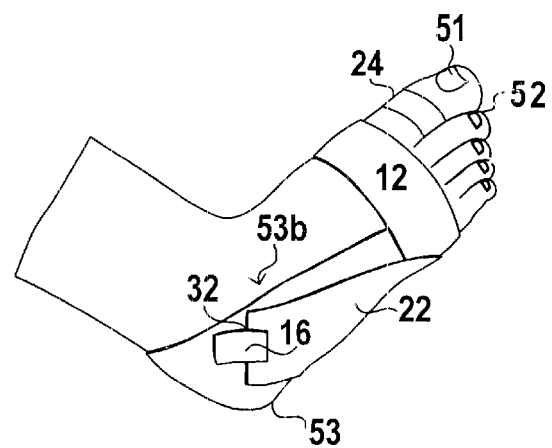

Following this, as shown in FIG. 6, the leg section 22 may be pulled from the bottom portion 55 of the foot 50 to the top portion 54 as by wrapping it around the outer side portion 58b of the foot 50, preferably maintaining a snug tension in the strap member 12 and avoiding wrinkling of the strap member 12. Finally, with reference to FIG. 7, the leg section 22 is directed across the top portion 54 of the foot 50 towards the big toe 51, back around the bottom portion 55 of the foot 50 proximal to the metatarsal phalangeal joints and adjacent the bottom of the big toe 51 and then toward the outer portion 53b of the heel 53. The end 32 of the leg section is preferably adjacent the outer portion 53b of the heel 53 and secured in this orientation using the fastening member 16. If the strap member 12 is too long to enable this positioning of the end 32, the leg section 22 may be shortened, as by cutting with scissors, so that the end 32 may be positioned in the desired orientation.

The strap system of the invention is intended for use under the direction and supervision of a physician or other appropriate health care provider for treating conditions associated with excessive foot pronation by reducing excessive pronation by urging the calcaneus (heel bone) of the foot inward. Also, the strap substantially locks the first ray, talonavicular, calcaneocuboid, navicular cuboid joints and the first metatarso-phalangeal joints in a desired orientation, such as a plantar-flexed orientation. This is believed to promote a neutral alignment of the heel, reduce subtalar joint pronation and aid in stabilizing the mid-tarsal joint of the foot during midstance of the gait cycle. The strap substantially positions the first ray (i.e. big toe joint) in a desired orientation, such as a plantar flexed orientation. The combination of controlling subtalar joint pronation and plantar flexion of the first ray, stabilizes the talonavicular, calcaneocuboid joints as well as engaging and locking a facet between the navicular and cuboid thus stabilizing the foot during the heel lift and push off phases of the gait. In addition, the cushioning properties of the strap member aid in reducing impact to the heel and offer support to the arch of the foot.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A device for treating conditions associated with excessive pronation of the subtalar joint of a human foot of the type having a heel bone and a toe, the device comprising a substantially T-shaped strap member having an elongate leg section having a first end and an opposite second end, the leg section being positionable to wrap around the heel bone, a head section substantially transverse to the leg section and located at the second end of the strap member, the head section being configured so as to be positionable to substantially wrap around a width portion of the toe of the human foot, and a first fastener associated with the head section for maintaining it in a wrapped orientation around the width of the toe, wherein when the strap member is secured in a wrapped orientation with the leg section around the heel bone and the head section wrapped around the width portion of the toe, the strap member urges the heel bone in an inward direction to stabilize the foot during ambulation and inhibit excessive pronation of the foot.

2. The device of claim 1, wherein the strap member is substantially elastic and flexible.

3. The device of claim 1, wherein the strap member has a fabric covering over foam.

4. The device of claim 1, wherein the head section is configured to wrap around is a big toe of the foot.

5. A system for treating conditions associated with excessive pronation of the subtalar joint of a human foot of the type having a heel bone and a toe, the system comprising a substantially T-shaped strap member having an elongate leg section having a first end and opposite second end, the leg section being positionable to wrap around the heel bone, a head section substantially transverse to the leg section and located at the second end of the strap member, the head section being configured so as to be positionable to substantially wrap around a width portion of the toe of the human foot, one or more fastener members attachable to portions of the strap member for maintaining adjacent portions of the strap member in a desired position relative to one another and the strap member in a tensioned state when the strap member is in use such that the leg section is wrapped around the heel bone and the head section is wrapped around the width portion of the toe, and the tension applied by the strap member urges the heel bone in an inward direction to stabilize the foot during ambulation and inhibit excessive pronation of the foot.

6. The system of claim 1, wherein the one or more fastener members comprises a first fastener member positionable to span between and secure first and second strap portions positioned during use of the strap member in an orientation wherein they are located in an overlapped orientation relative to the big toe.

7. A method for treating conditions associated with excessive pronation of the subtalar joint of a human foot of the type having a heel bone and a toe, the method comprising the steps of providing a strap comprising a substantially T-shaped strap member having an elongate leg section having a first end and an opposite second end, a head section substantially transverse to the leg section and located at the second end of the strap member, the head section being configured so as to be positionable to substantially wrap around a width portion of the toe, and a first fastener associated with the head section for maintaining it in a wrapped orientation around the width of the toe, positioning the head section of the strap about the width of the toe of the foot and the leg section about the heel bone and securing the strap member in a wrapped orientation with the leg section around the heel bone and the head section wrapped around the width portion of the toe, exerting a tension on the strap so as to urge the heel bone in an inward direction, and securing the leg section of the strap adjacent the foot so as to maintain the tension on the strap to stabilize the foot during ambulation and inhibit excessive pronation of the foot.

8. The method of claim 7, wherein the toe comprises a big toe and the desired orientation is a plantar-flexed orientation.

* * * * *